(12) United States Patent
Krug

(10) Patent No.: US 10,674,980 B2
(45) Date of Patent: Jun. 9, 2020

(54) GANTRY FOR A MEDICAL IMAGING FACILITY AND METHOD FOR AIR COOLING OF AT LEAST ONE COMPONENT OF THE GANTRY

(71) Applicant: Siemens Healthcare GmbH, Erlangen (DE)

(72) Inventor: Rita Krug, Fuerth (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 69 days.

(21) Appl. No.: 16/006,983

(22) Filed: Jun. 13, 2018

(65) Prior Publication Data
US 2018/0368794 A1 Dec. 27, 2018

(30) Foreign Application Priority Data
Jun. 21, 2017 (EP) ..................................... 17177191

(51) Int. Cl.
*A61B 6/00* (2006.01)
*A61B 6/03* (2006.01)
*A61B 5/055* (2006.01)

(52) U.S. Cl.
CPC ............ *A61B 6/4488* (2013.01); *A61B 6/032* (2013.01); *A61B 6/035* (2013.01); *A61B 6/4447* (2013.01); *A61B 5/055* (2013.01); *A61B 6/037* (2013.01)

(58) Field of Classification Search
None
See application file for complete search history.

(56) References Cited

U.S. PATENT DOCUMENTS

| 6,289,073 | B1 | 9/2001 | Sasaki et al. |
| 6,988,827 | B2 | 1/2006 | Mueller |
| 7,374,338 | B2 | 5/2008 | Distler et al. |
| 7,410,295 | B2 | 8/2008 | Distler et al. |
| 2009/0041181 | A1 | 2/2009 | Krug |
| 2014/0378817 | A1 | 12/2014 | Gregerson et al. |
| 2015/0320376 | A1* | 11/2015 | Oishi ................... A61B 6/4405 378/199 |
| 2016/0235378 | A1 | 8/2016 | Yun et al. |

FOREIGN PATENT DOCUMENTS

DE 102007037313 A1 2/2009

OTHER PUBLICATIONS

Extended European Search Report 17177191.8 dated Dec. 15, 2017.

* cited by examiner

*Primary Examiner* — Hoon K Song
(74) *Attorney, Agent, or Firm* — Harness, Dickey & Pierce, P.L.C.

(57) ABSTRACT

A gantry is for a medical imaging facility. An air inflow surface, for air cooling of at least one component of the gantry, is embodied on an outer surface of the gantry. In an operating state of the gantry, the gantry is delimited to the top in an area of the air inflow surface by the air inflow surface.

28 Claims, 4 Drawing Sheets

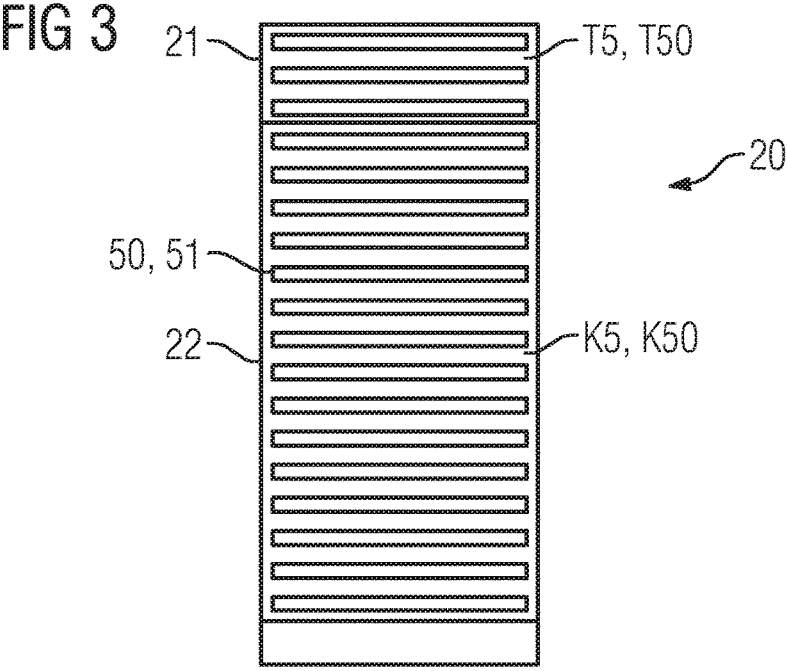
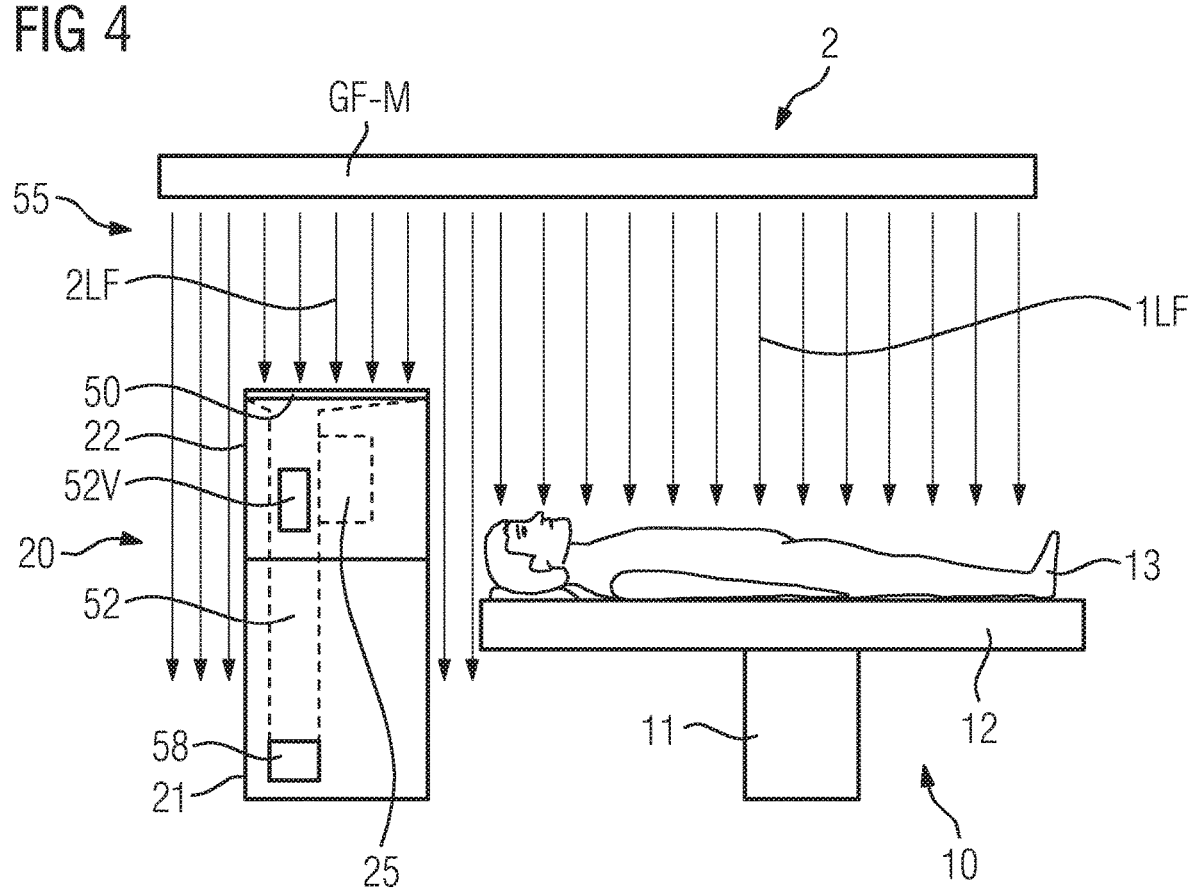

GANTRY FOR A MEDICAL IMAGING FACILITY AND METHOD FOR AIR COOLING OF AT LEAST ONE COMPONENT OF THE GANTRY

PRIORITY STATEMENT

The present application hereby claims priority under 35 U.S.C. § 119 to European patent application number EP17177191.8 filed Jun. 21, 2017, the entire contents of which are hereby incorporated herein by reference.

FIELD

At least one embodiment of the invention generally relates to a gantry for a medical imaging facility, a medical imaging facility, an arrangement and/or a method for air cooling of at least one component of a gantry of a medical imaging facility.

BACKGROUND

Computed tomography devices can for example be cooled by air. In such cases this provides the opportunity on the one hand of letting the air circulate in a closed circuit in the gantry. In this system the air circulates in a closed circuit and is cooled down by a heat exchanger, for example water. On the other hand the air from the examination room can be sucked in via openings in cladding of the computed tomography device (CT device) for the purpose of cooling and can be emitted heated up again to the room.

In an intervention room or operating room there are mostly specific air flow conditions in existence, which are embodied in particular in accordance with the teaching of clean room technology. In such situations air flows from the ceiling to the floor around the patient and in this way forms a germ-free environment in the vicinity of the patient. This air flow is aligned, has a speed of flow of between 0.2 and 0.3 meters per second for example, is predominantly laminar and is referred to below as low-turbulence displacement flow, abbreviated in German to TAV. TAV is also known to the person skilled in the art by the terms laminar flow and laminar air flow.

The TAV must not be disturbed by the cooling of the CT device. Depending on how the room in which the CT device is set up is equipped, and how the CT device is used, a relatively large field is provided with TAV, which with a usual size of three meters by three meters for example can also comprise an operating instrument table for example, or a relatively small field is provided, which is essentially restricted to the operating area on the patient.

If the CT device is now not located outside the TAV field, but is located in this field or only partly in this field, then a displacement and deflection of the flow takes place on the surfaces of the CT device. In this case the CT device forms an obstacle to the flow. Moreover the sucking in and blowing out of the air at respective surfaces of the cladding of the CT device means that the TAV flow is likewise influenced.

The possible consequences thereof are for example an increased speed of flow, which in particular can be attributed to the displacement effect of the CT device as a body in the flow, an increased deflection of the flow and also an increased flow breakup, which can be attributed in particular to an unfavorable outer contour of the CT device. All three effects lead to the disturbance of the TAV by turbulences.

U.S. Pat. No. 6,988,827 B2 discloses a cooling system for a gantry of a CT device.

U.S. Pat. No. 7,374,338 B2 discloses a cooling system for a gantry of a CT device.

U.S. Pat. No. 7,410,295 B2 discloses a cooling system for a gantry of a CT device.

US 2014/0378817 A1 discloses a cooling system for a CT device, in which the air inflow opening and the air outflow openings are arranged relatively far down, wherein the air exiting from the CT device is directed via the air outflow opening below a sterile field for surgical interventions. Because of the displacement effect of the CT device this can result in a significant disturbance of the TAV however.

SUMMARY

For application in the operating area water-cooled CT devices are often used, with which an exchange of air with the room can be avoided. The inventor has recognized, however, that the routing of the water hoses can restrict free movement in the room.

At least one embodiment of the invention provides air cooling of a gantry of a medical imaging facility, which uses the air in the room, which surrounds the gantry and which is improved in relation to air flow conditions. Further advantageous aspects of the invention are taken into account in the claims.

At least one embodiment of the invention relates to a gantry for a medical imaging facility, wherein an air inflow surface for air cooling of at least one component of the gantry is embodied in an outer surface of the gantry, wherein, in an operating state of the gantry, the gantry is delimited to the top by the air inflow surface in an area of the air inflow surface.

At least one embodiment of the invention further relates to a medical imaging facility having a gantry in accordance with at least one of the embodiments disclosed in this application.

At least one embodiment of the invention further relates to an arrangement having a gantry in accordance with at least one of the embodiments disclosed in this application and to an airflow generation unit.

At least one embodiment of the invention further relates to a method for air cooling of at least one component of a gantry of a medical imaging facility, the method comprising:
Generation of a laminar air flow, wherein at least one gantry part air flow of the laminar air flow flows from above onto the gantry,
Receiving of the at least one gantry part air flow into a cooling duct of the gantry via an air inflow surface, which is embodied on an outer surface of the gantry and which in an area of the air inflow surface delimits the gantry to the top, wherein a cooling air flow is generated, which flows through the cooling duct, and
Cooling of the at least one component of the gantry via the cooling air flow.

BRIEF DESCRIPTION OF THE DRAWINGS

The invention will be explained below with reference to example embodiments, which refer to the enclosed figures. The representation in the figures is schematic, greatly simplified and not necessarily true-to-scale.

In the figures:

FIG. 3 shows a schematic view of an example embodiment of an inventive gantry in an orthogonal projection from above, FIG. 4 shows a schematic view of an example embodiment of an inventive arrangement.

DETAILED DESCRIPTION OF THE EXAMPLE EMBODIMENTS

Figure 1:
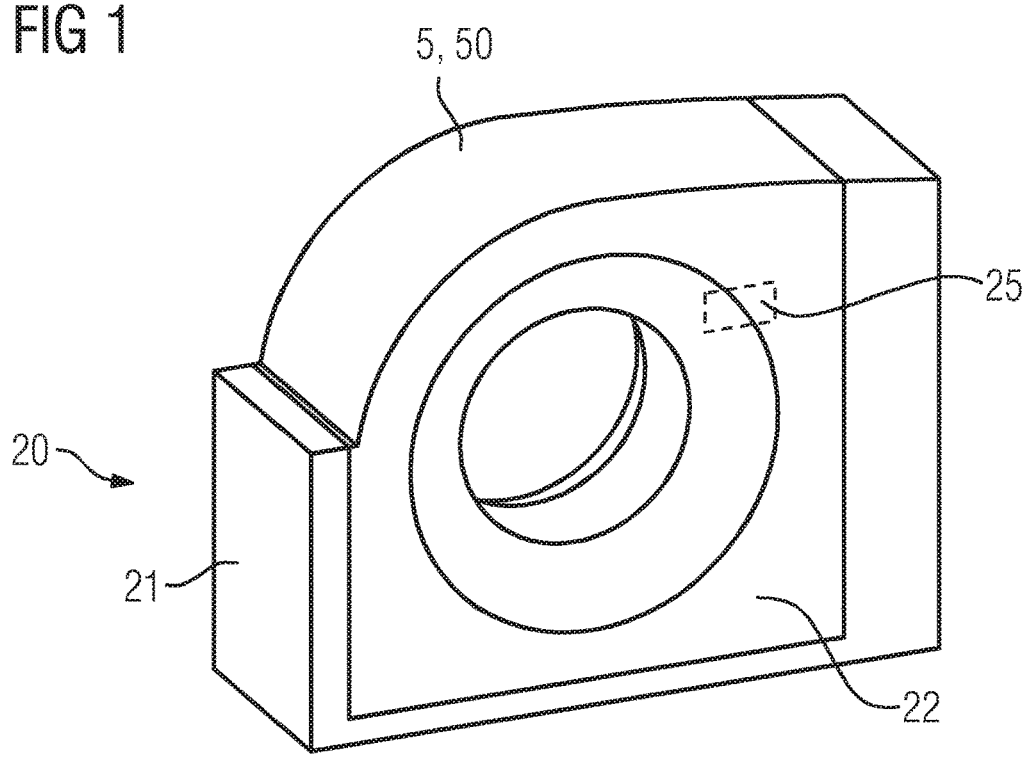
FIG. 1 shows a schematic view of an example embodiment of an inventive gantry for a medical imaging facility.
Figure 2:
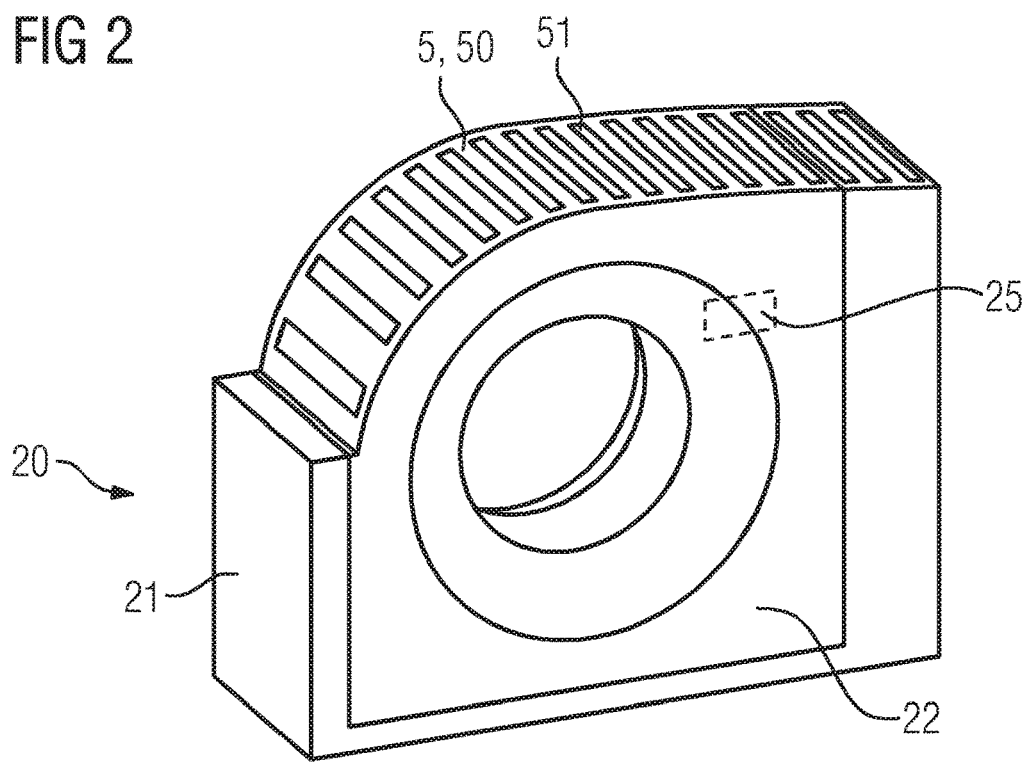
FIG. 2 shows a schematic view of an example embodiment of an inventive gantry for a medical imaging facility.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects.

Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention relates to a gantry for a medical imaging facility, wherein an air inflow surface for air cooling of at least one component of the gantry is embodied in an outer surface of the gantry, wherein, in an operating state of the gantry, the gantry is delimited to the top by the air inflow surface in an area of the air inflow surface.

In at least one embodiment, in the operating state of the gantry, the gantry can essentially be delimited to the top by the air inflow surface.

In at least one embodiment, in an orthogonal projection from above, the air inflow surface can form at least 50 percent, in particular at least 70 percent, preferably at least 90 percent, of the outer surface of the gantry.

In at least one embodiment, the gantry can have a cooling duct for the air cooling of the at least one component of the gantry, wherein, in the operating state of the gantry, the air inflow surface is embodied such that an air flow, in particular a laminar air flow flowing vertically from above onto the gantry, can flow through the air inflow surface into the cooling duct with low turbulence.

In at least one embodiment, the air inflow surface can be embodied for an average speed of air inflow of 0.2 to 0.3 meters per second.

In at least one embodiment, a planar distribution of an air inflow parameter in the air inflow surface can be adapted to a slope of the outer surface of the gantry such that the air inflow parameter, in an orthogonal projection from above, has an essentially even planar distribution.

In at least one embodiment, the air inflow surface can have an air inflow element, which is chosen from the group that consists of an air filter, an aperture plate, an inflow slat and combinations thereof.

In at least one embodiment, the air inflow parameter can be selected from the air inflow parameter group that consists of a pressure loss coefficient, an opening spacing, an opening surface and combinations thereof.

In at least one embodiment, the gantry can have an air outflow surface for the air cooling of the at least one component of the gantry, wherein the air outflow surface and the air inflow surface are connected to one another via a cooling duct.

In at least one embodiment,
  the gantry has a stationary support frame and a tilting frame,
  the outer surface, in an area of the support frame, has a support frame outer surface,
  the outer surface, in an area of the tilting frame, has a tilting frame outer surface, and/or
  a support frame part surface of the air inflow surface is embodied in the support frame outer surface and/or wherein a tilting frame part surface of the air inflow surface is embodied in the tilting frame outer surface.

At least one embodiment of the invention further relates to a medical imaging facility having a gantry in accordance with at least one of the embodiments disclosed in this application.

At least one embodiment of the invention further relates to an arrangement having a gantry in accordance with at least one of the embodiments disclosed in this application and to an airflow generation unit.

In at least one embodiment, the gantry can be in an operating state of the gantry in which in the area of the air inflow surface the gantry is delimited to the top by the air inflow surface.

In at least one embodiment, the airflow generation unit can be embodied to generate the laminar air flow such that at least one gantry part air flow of the laminar air flow flows from above onto the gantry and flows into the gantry through the air inflow surface.

In at least one embodiment, the arrangement can further feature a patient support facility of the medical imaging facility.

In at least one embodiment, the airflow generation unit for generation of the laminar air flow can be embodied such that at least one patient part air flow of the laminar air flow flows from above onto the patient support facility.

In at least one embodiment, the arrangement can further have the medical imaging facility.

At least one embodiment of the invention further relates to a method for air cooling of at least one component of a gantry of a medical imaging facility, the method comprising:

Generation of a laminar air flow, wherein at least one gantry part air flow of the laminar air flow flows from above onto the gantry, Receiving of the at least one gantry part air flow into a cooling duct of the gantry via an air inflow surface, which is embodied on an outer surface of the gantry and which in an area of the air inflow surface delimits the gantry to the top, wherein a cooling air flow is generated, which flows through the cooling duct, and Cooling of the at least one component of the gantry via the cooling air flow.

In at least one embodiment, the air inflow surface can have a number of air filters with different pressure loss coefficients. In particular the air inflow surface can have a number of openings, for example in the form of holes and/or slots.

The opening spacing can, for example in at least one embodiment, involve the spacing between holes and/or slots. The opening surface can involve a cross-sectional surface of a hole and/or of a slot for example. In particular the air inflow surface can have a number of perforated sheets with different hole spacings. In particular the air inflow surface can have a number of inflow slots with different slot widths between immediately adjacent inflow slots.

The air inflow surface can, in at least one embodiment, be embodied in particular as a contiguous surface or can have a number of part air inflow surfaces separated from one another. The air inflow surface can in particular have areas that are permeable for air, and areas that are impermeable for air. For example an opening can form an area permeable for air. For example a material of the outer surface, which delimits the opening, can form an area impermeable for air.

In at least one embodiment, both the areas that are permeable for air and also the areas that are impermeable for air can be distributed evenly over the air inflow surface and/or over the outer surface. In accordance with one form of embodiment of the invention the entire air inflow surface is essentially permeable for air, in particular permeable. In accordance with one form of embodiment of the invention the areas that are permeable for air form at least 50 percent, in particular at least 70 percent, preferably at least 90 percent of the air inflow surface.

The air outflow surface can, in at least one embodiment, form an exhaust surface of the air cooling of the gantry. A disturbance of the TAV field can in particular be reduced by the air being exhausted where possible at the edge of the TAV field. For example the exhaust surface can be arranged to the side of the gantry or on a rear side of the gantry, which faces away from a support pedestal of the patient support facility. As an alternative or in addition the exhaust surface can be arranged in the lower area of the gantry and/or an air flow flowing out of the exhaust surface can be directed downwards via slots.

Furthermore a disturbance of the TAV field can, in at least one embodiment, be reduced in particular by an outer contour of the gantry being designed so as to favor the TAV flow. The outer contour of the gantry can in particular be designed so that edges, projections or sharp changes of contour are largely avoided or excluded in the direction of the TAV.

At least noe embodiment of the inventive solution in particular makes it possible to provide a gantry for a medical imaging facility that can be operated in a TAV field, wherein air from the TAF field is used for the air cooling of the gantry, wherein a disturbance of the TAV field is largely avoided. Moreover the inventive gantry can be moved in the TAV field in wide areas without there being any significant change to the influencing of the TAV field by the gantry.

The medical imaging facility, in embodiments, can be selected for example from the imaging modality group that consists of an x-ray device, a C-arm x-ray device, a computed tomography device (CT device), a molecular imaging device (MI device), a single photon emission computed tomography device (SPECT device), a positron emission device (PET device), a magnetic resonance tomography device (MR device) and combinations thereof, in particular a PET-CT device and a PET-MR device. The medical imaging facility can further have a combination of an imaging modality, which is selected for example from the imaging modality group, and a radiotherapy modality. In this case the radiotherapy modality can feature an irradiation unit for therapeutic irradiation for example.

Without restricting the general inventive idea, in a few of the forms of embodiment a computed tomography device is given as an example for a medical imaging facility.

In accordance with one form of embodiment of the invention the medical imaging facility has an acquisition unit, which is embodied for acquisition of the acquisition data. In particular the acquisition unit can have a radiation source and a radiation detector. One form of embodiment of the invention makes provision for the radiation source to be embodied for emission and/or for excitation of radiation, in particular electromagnetic radiation, and/or for the radiation detector to be embodied for the detection of the radiation, in particular of the electromagnetic radiation. The radiation can for example arrive from the radiation source at a region to be imaged and/or, after an interaction with the region to be imaged, can arrive at the radiation detector.

In the interaction of the radiation with the region to be imaged the radiation is modified and thus becomes a carrier of information that relates to the region to be imaged. In the interaction of the radiation with the detector this data is acquired in the form of acquisition data.

With a computed tomography device in particular and with a C-arm x-ray device the acquisition data can be projection data, the acquisition unit a projection data acquisition unit, the radiation source an x-ray source, the radiation detector an x-ray detector. The x-ray detector can in particular be a quanta-counting and/or energy-resolving x-ray detector.

With a magnetic resonance tomography device in particular the acquisition data can be a magnetic resonance dataset, the acquisition unit a magnetic resonance data acquisition unit, the radiation source a first radio frequency antenna unit, the radiation detector the first radio frequency antenna unit and/or a second radio frequency antenna unit.

The gantry of a medical imaging facility typically has a support structure on which in particular components of the acquisition unit, in particular the radiation source and/or the radiation detector, are arranged. The support structure of the gantry typically has a rigidity and strength such as to enable the components of the acquisition unit to be arranged both relative to one another and also relative to a region to be imaged in a geometry sufficiently defined for the imaging.

With a computed tomography device the gantry typically has a support frame and a rotor supported to allow rotation relative to the support frame, wherein the radiation source and the radiation detector are arranged on the rotor. Optionally the gantry can have a tilting frame supported to allow tilting relative to the support frame, wherein the rotor is arranged on the tilting frame.

With a C-arm x-ray device the gantry typically has a support frame and a C-arm supported to allow pivoting relative to the support frame, wherein the radiation source and the radiation detector are arranged on the C-arm.

With a magnetic resonance tomography device the gantry typically has a support frame on which the main magnet and a first radio frequency antenna unit are arranged, wherein the first radio frequency antenna unit is embodied in the form of a coil known to the person skilled in the art as a body coil.

Within the framework, the invention features that are described in relation to different forms of embodiment of the invention and/or different categories of claims (method, use, facility, system, arrangement etc.), can be combined into further forms of embodiment of the invention. For example a claim or embodiment that relates to a method can also be developed with features that are described or claimed in conjunction with a facility and vice versa. Functional features of a method in this case can be embodied by correspondingly embodied physical components. Along with the forms of embodiment of the invention explicitly described in this application numerous further forms of embodiment of the invention are conceivable, which can be arrived at by the person skilled in the art without departing from the area of the invention, provided it is specified by the claims.

The use of the indefinite article "a" or "an" does not exclude the feature concerned also being able to be present a number of times. The use of the expression "has" does not exclude terms linked by the expression "has" being able to be identical. For example the medical imaging facility has the medical imaging facility. The use of the expression "unit" does not exclude the object to which the expression "unit" refers being able to feature a number of components that are separated physically from one another.

The example embodiment of an inventive gantry 20 for a medical imaging facility 1 shown in FIG. 1 has an outer surface 5. The outer surface 5 can in particular be formed by cladding of the gantry 20. The cladding can be mounted for example on a support structure and/or be embodied self-supporting, in particular forming a support structure itself.

Embodied in the outer surface 5 of the gantry 20 is an air inflow surface 50 for air cooling of at least one component 25 of the gantry 20. In the operating state of the gantry 20, which is shown in FIG. 1, the gantry 20 is delimited to the top in an area of the air inflow surface 50 by the air inflow surface 50. The gantry 20 is essentially delimited to the top by the air inflow surface 50. The at least one component 25 can involve a radiation source 26 and/or a detector 28 for example.

The example embodiment of an inventive gantry 20 for a medical imaging facility 1 shown in FIG. 1 has an air inflow surface 50 with air inflow elements 51 in the form of air inflow slots. The arrangement of the air inflow slots enables an even air inflow to be realized, in particular such that a vertical component of the air inflow speed corresponds to the speed of flow of the laminar air flow 55. The spacing between two immediately adjacent air inflow slots is greater in areas in which the outer surface 5 of the gantry 20 has a steep slope than it is in areas in which the outer surface 5 of the gantry 20 has a gentle slope.

In the orthogonal projection from above into a horizontal plane, which is shown in FIG. 3, the air inflow surface 50 essentially forms the entire outer surface 5 of the gantry 20. The air inflow surface 50 in particular receives from above the gantry part air flow 2LF of the laminar air flow 55 flowing vertically from above onto the gantry 20 evenly distributed over essentially the entire part of the outer surface 5, which delimits the gantry 20 to the top. In the orthogonal projection shown the spacing between the immediately adjacent air inflow slots is essentially the same for all air inflow slots.

The air inflow surface 50 projected into the horizontal has an average air inflow speed of 0.2 to 0.3 meters per second. The volume of cooling air that flows through the cooling duct 52 corresponds to the volume flow that is produced when the surface of the orthogonal projection of the air inflow surface 50 from above into a horizontal plane is multiplied by the air inflow speed.

The gantry 20 can in particular be embodied such that this volume of cooling air is sufficient for the air cooling of the at least one component with a typical loading and/or at a maximum loading of the at least one component. In particular the medical imaging facility 1 can be embodied such that the at least one gantry part air flow 2LF of the laminar air flow 55 flows continuously into the gantry 20, in particular even if the medical imaging facility 1 is in a standby state.

FIG. 4 shows a schematic view of an example embodiment of an inventive arrangement 2. The arrangement 2 has the gantry 20 and an airflow generation unit GF-M. The airflow generation unit GF-M generates the laminar air flow 55 such that at least one gantry part air flow 2LF of the laminar air flow 55 flows from above onto the gantry 20 and flows into the gantry 20 through the air inflow surface 50.

The gantry 20 has a cooling duct 52 for air cooling of the at least one component 25 of the gantry 20, wherein the air inflow surface 50, in the operating state of the gantry 20, is embodied such that a laminar air flow 55 flowing from above onto the gantry 20 can flow into the cooling duct 52 through the air inflow surface 50 with low turbulence.

This means that the displacement effect of the gantry on the TAV field 55 is relatively small. An air pump 52 is located in the cooling duct 52, which in the area of the air inflow surface 50 can suck cooling air into the cooling duct 52 and/or, in the area of the air outflow surface 58, can blow out the heated cooling air. The cooling duct 52 is expanded in a funnel shape in an area adjoining the air inflow surface 50. The air inflow surface 50 can thus also be referred to as the air intake surface.

The arrangement further has a patient support facility 10 of the medical imaging facility 1, wherein the airflow generation unit GF-M for generation of the laminar air flow 55 is embodied such that at least one patient part air flow 1LF of the laminar air flow 55 in particular flows vertically from above onto the patient support facility 10.

Figure 5:
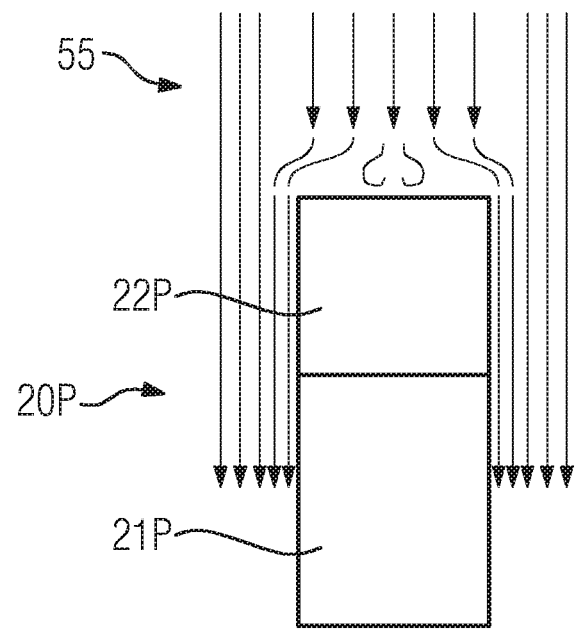
FIG. 5 shows a schematic view of a conventional gantry in a TAV field.

FIG. 5 shows a schematic view of a conventional gantry 20P in a TAV field 55. In the areas with arrows lying close to one another, because of the displacement effect, the speed of flow is relatively high, so that a disturbance of the TAV is present. An especially strong disturbance of the TAV can arise if the cooling air flows out onto the upwards-facing outer surface of the gantry.

Figure 6:
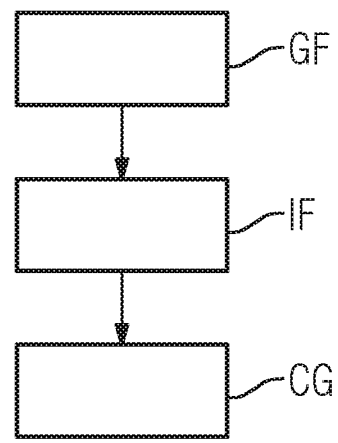
FIG. 6 shows a block schematic of an example embodiment of an inventive method for air cooling.

FIG. 6 shows a block diagram of an example embodiment of an inventive method for air cooling, the method comprising:

Generation GF of a laminar air flow 55, wherein at least one gantry part air flow 2LF of the laminar air flow 55 flows from above onto the gantry 20, Receiving IF of the at least one gantry part air flows 2LF into a cooling duct 52 of the gantry 20 via an air inflow surface 50 which is embodied on an outer surface 5 of the gantry 20 and which delimits the gantry 20 to the top in an area of the air inflow surface 50, wherein a flow of cooling air CF is generated, which flows through the cooling duct 52, and Cooling CG of the at least one component 25 of the gantry 20 via the cooling air flow CF.

Figure 7:
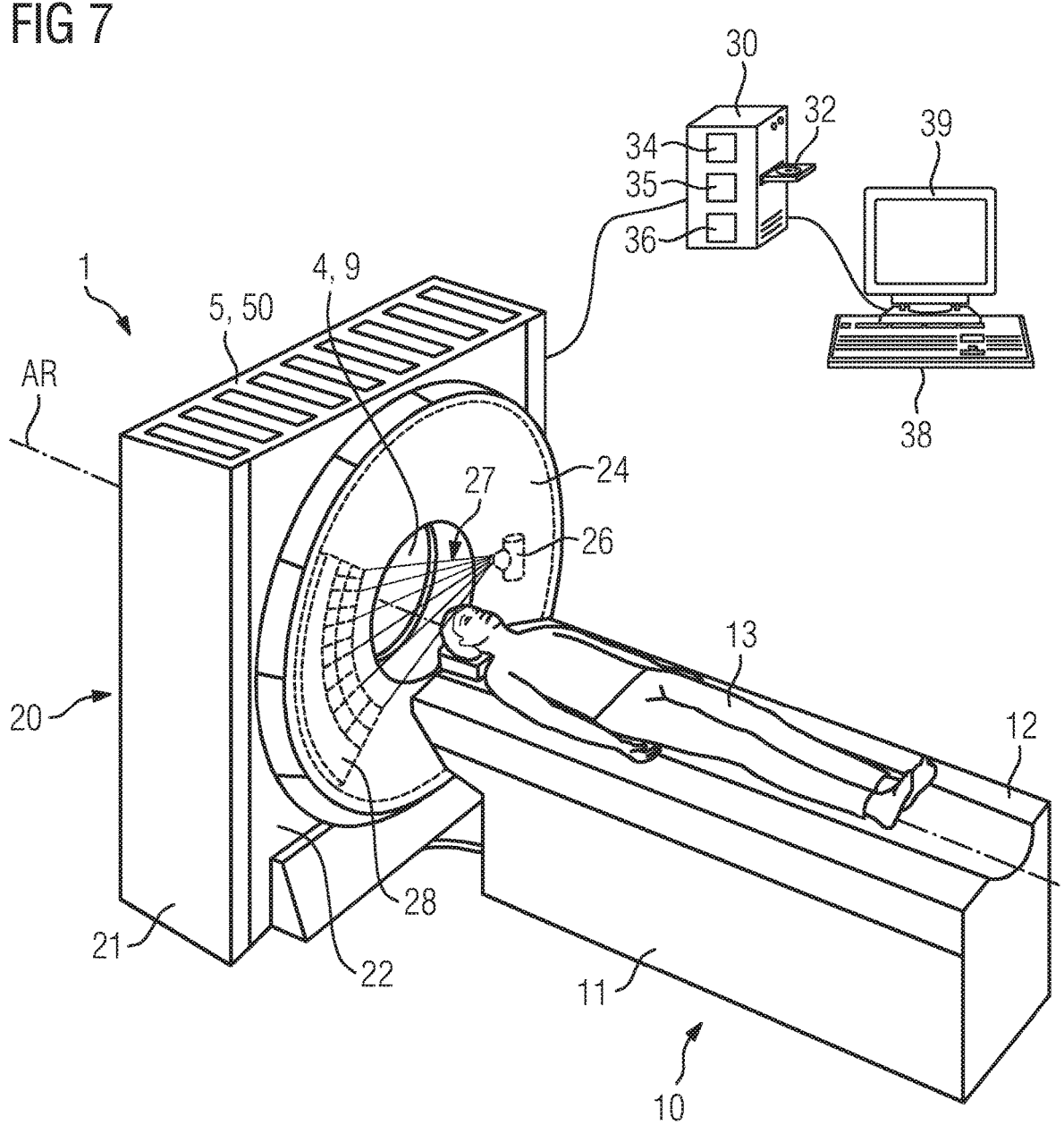
FIG. 7 shows a schematic view of an example embodiment of an inventive medical imaging facility.

FIG. 7 shows a schematic view of an example embodiment of an inventive medical imaging facility 1. Without restricting the general inventive idea, a computed tomography device is shown by way of example for the medical imaging facility 1. The medical imaging facility 1 has the gantry 20, the tunnel-shaped opening 9, the patient support facility 10 and the control facility 30.

The gantry 20 has the stationary support frame 21, the tilting frame 22 and the rotor 24. The tilting frame 22 is arranged to allow it to tilt via a tilt support facility on the stationary support frame 21 about an essentially horizontal tilt axis relative to the stationary support frame 21. The rotor 24 is arranged to allow it to rotate relative to the tilting frame 22 about an axis of rotation AR via a rotational support facility on the tilting frame 22. The axis of rotation AR is essentially perpendicular to the tilt axis and essentially parallel to the longitudinal direction of the support plate 12. The operating state of the gantry 20, in which the gantry 20 is delimited to the top in an area of the air inflow surface 50 by the air inflow surface 50, can for example be an operating state in which the axis of rotation AR is essentially horizontal, in particular horizontal. The outer surface 5 of the gantry 20 can in particular involve an outer surface 5 of the gantry 20, which faces away from the tunnel-shaped opening 9.

The patient 13 can be introduced into the tunnel-shaped opening 9. Located in the tunnel-shaped opening 9 is the acquisition area 4. In the acquisition area 4 a region of the patient 13 to be imaged is able to be positioned such that the radiation 27 from the radiation source 26 can arrive at the region to be imaged and after an interaction with the region to be imaged can arrive at the radiation detector 28.

The patient support facility 10 has the support pedestal 11 and the support plate 12 to support the patient 13. The support plate 12 is arranged relative to the support pedestal 11 to allow movement on the support pedestal 11 such that the support plate 12, in a longitudinal direction of the support plate 12, is able to be introduced into the acquisition area 4.

The medical imaging facility 1 is embodied for acquisition of acquisition data based on electromagnetic radiation 27. The medical imaging facility 1 has an acquisition unit. The acquisition unit is a projection data acquisition unit with the radiation source 26, e.g. an x-ray source, and the detector 28, e.g. an x-ray detector, in particular an energy-resolving x-ray detector. The radiation source 26 is arranged on the rotor 24 and embodied for emission of radiation 27, e.g. x-ray radiation, with radiation quanta 27. The detector 28 is arranged on the rotor 24 and embodied for detection of the radiation quanta 27. The radiation quanta 27 can arrive at the area of the patient 13 to be imaged from the radiation source 26 and after an interaction with the area to be imaged, can arrive at the detector 28. In this way acquisition data of the area to be imaged can be acquired in the form of projection data via the acquisition unit.

The control facility 30 is embodied for receiving the acquisition data acquired by the acquisition unit. The control facility 30 is embodied for controlling the medical imaging facility 1. In particular the airflow generation unit GF-M can also be controlled via the control facility 30. The control facility 30 has the data processing unit 35, the computer-readable medium 32 and the processor system 36. The control facility 30, in particular the data processing unit 35, is formed by a data processing system, which has a computer.

The control facility 30 has the image reconstruction facility 34. Based on the acquisition data, a medical image dataset can be reconstructed via the image reconstruction facility 34. The medical imaging facility 1 has an input facility 38 and an output facility 39, which are each connected to the control facility 30. The input facility 38 is embodied for input of control information, e.g. image reconstruction parameters, examination parameters or the like. The output facility 39 is in particular embodied for output of control information, images and/or acoustic signals.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A gantry for a medical imaging facility, comprising:
an air inflow surface to cool air of at least one component of the gantry, embodied in an outer surface of the gantry, wherein, in an operating state of the gantry, the gantry includes the air inflow surface on a top portion of an outer surface of the gantry;
a stationary support frame; and
a tilting frame, the outer surface of the gantry, in an area of the support frame, including a stationary support frame outer surface and the outer surface of the gantry, in an area of the tilting frame, including a tilting frame outer surface,
wherein at least one of
a support frame part surface of the air inflow surface is embodied in the support frame outer surface, and
a tilting frame part surface of the air inflow surface is embodied in the tilting frame outer surface.

2. The gantry of claim 1, wherein, in the operating state of the gantry, the gantry is essentially delimited to the top by the air inflow surface.

3. The gantry of claim 1, wherein, in an orthogonal projection from above, the air inflow surface forms at least 50 percent of the outer surface of the gantry.

4. The gantry of claim 1, further comprising:
a cooling duct to cool air of the at least one component of the gantry, wherein the air inflow surface, in the operating state of the gantry, is embodied such that a laminar flow of air flowing onto the gantry from above flows into the cooling duct through the air inflow surface with relatively low turbulence.

5. The gantry of claim 1, wherein the air inflow surface is embodied for an average air inflow speed of 0.2 to 0.3 meters per second.

6. The gantry of claim 1, wherein a planar distribution of an air inflow parameter in the air inflow surface is adapted to a slope of the outer surface of the gantry such that the air inflow parameter, in an orthogonal projection from above, has an essentially even planar distribution.

7. The gantry of claim 1, wherein the air inflow surface includes an air inflow element, selected from a group consisting of an air filter, an aperture plate, an inflow slat, a combination of an air filter and an aperture plate, a combination of an air filter and an inflow slat, a combination of an aperture plate and an inflow slat, and a combination of an air filter, an aperture plate and an inflow slat.

8. The gantry of claim 6, wherein the air inflow parameter is selected from a group consisting of a pressure loss coefficient, an opening spacing, an opening surface, a combination of a pressure loss coefficient and an opening spacing, a combination of a pressure loss coefficient and an opening surface, a combination of an opening spacing and an opening surface, and a combination of a pressure loss coefficient, an opening spacing, and an opening surface.

9. The gantry of claim 1, further comprising:
an air outflow surface for the air cooling of the at least one component of the gantry, the air outflow surface and the air inflow surface being connected via a cooling duct.

10. A medical imaging facility, comprising the gantry of claim 1.

11. An arrangement, comprising:
the gantry of claim 1, the gantry, in an operating state, being delimited to the top in the area of the air inflow surface by the air inflow surface; and
an airflow generation unit to generate laminar air flow, configured such that at least one gantry part air flow of the laminar air flow flows from above onto the gantry and flows into the gantry through the air inflow surface.

12. The arrangement of claim 11, further comprising:
a patient support facility of the medical imaging facility, wherein the airflow generation unit for generating the laminar air flow is embodied such that, at least one patient part air flow of the laminar air flow flows from above onto the patient support facility.

13. The arrangement of claim 12, further comprising the medical imaging facility.

14. A method for air cooling of at least one component of a gantry of a medical imaging facility, the method comprising:
generating a laminar air flow, at least one gantry part air flow of the laminar air flow flowing from above onto the gantry;
receiving the at least one gantry part air flow from above into a cooling duct of the gantry, via an air inflow surface included on a top portion of an outer surface of the gantry, evenly distributed over essentially the entire part of the air inflow surface, the gantry including a stationary support frame and a tilting frame, the outer surface of the gantry, in an area of the support frame, including a stationary support frame outer surface and the outer surface of the gantry, in an area of the tilting frame, including a tilting frame outer surface, wherein at least one of
a support frame part surface of the air inflow surface is embodied in a support frame outer surface, and
a tilting frame part surface of the air inflow surface is embodied in the tilting frame outer surface;
generating a flow of cooling air from the at least one gantry part air flow received, to flow through the cooling duct; and
cooling the at least one component of the gantry via the flow of cooling air generated.

15. The gantry of claim 2, wherein, in an orthogonal projection from above, the air inflow surface forms at least 50 percent of the outer surface of the gantry.

16. The gantry of claim 2, further comprising:
a cooling duct to cool air of the at least one component of the gantry, wherein the air inflow surface, in the operating state of the gantry, is embodied such that a laminar flow of air flowing onto the gantry from above flows into the cooling duct through the air inflow surface with relatively low turbulence.

17. The gantry of claim 3, further comprising:
a cooling duct to cool air of the at least one component of the gantry, wherein the air inflow surface, in the operating state of the gantry, is embodied such that a laminar flow of air flowing onto the gantry from above flows into the cooling duct through the air inflow surface with relatively low turbulence.

18. The gantry of claim 2, wherein the air inflow surface is embodied for an average air inflow speed of 0.2 to 0.3 meters per second.

19. The gantry of claim 2, wherein a planar distribution of an air inflow parameter in the air inflow surface is adapted to a slope of the outer surface of the gantry such that the air inflow parameter, in an orthogonal projection from above, has an essentially even planar distribution.

20. The gantry of claim 2, wherein the air inflow surface includes an air inflow element, selected from the group consisting of an air filter, an aperture plate, an inflow slat, a combination of an air filter and an aperture plate, a combination of an air filter and an inflow slat, a combination of an aperture plate and an inflow slat, and a combination of an air filter, an aperture plate and an inflow slat.

21. The gantry of claim 2, further comprising:
an air outflow surface for the air cooling of the at least one component of the gantry, the air outflow surface and the air inflow surface being connected via a cooling duct.

22. The gantry of claim 4, further comprising:
an air outflow surface for the air cooling of the at least one component of the gantry, the air outflow surface and the air inflow surface being connected via the cooling duct.

23. A medical imaging facility, comprising the gantry of claim 2.

24. A medical imaging facility, comprising the gantry of claim 4.

25. An arrangement, comprising:
the gantry of claim 2, the gantry, in an operating state, being delimited to the top in the area of the air inflow surface by the air inflow surface; and
an airflow generation unit to generate laminar air flow, configured such that at least one gantry part air flow of the laminar air flow flows from above onto the gantry and flows into the gantry through the air inflow surface.

26. An arrangement, comprising:
the gantry of claim 4, the gantry, in an operating state, being delimited to the top in the area of the air inflow surface by the air inflow surface; and
an airflow generation unit to generate laminar air flow, configured such that at least one gantry part air flow of the laminar air flow flows from above onto the gantry and flows into the gantry through the air inflow surface.

27. An arrangement, comprising:
the gantry of claim 1, the gantry, in an operating state, being delimited to the top in the area of the air inflow surface by the air inflow surface; and
an airflow generation unit to generate laminar air flow, configured such that at least one gantry part air flow of the laminar air flow flows from above onto the gantry and flows into the gantry through the air inflow surface.

28. The gantry of claim 7, wherein a planar distribution of an air inflow parameter in the air inflow surface is adapted to a slope of the outer surface of the gantry such that the air inflow parameter, in an orthogonal projection from above, has an essentially even planar distribution, and wherein the air inflow parameter is selected from a group consisting of a pressure loss coefficient, an opening spacing, an opening surface, a combination of a pressure loss coefficient and an opening spacing, a combination of a pressure loss coefficient and an opening surface, a combination of an opening spacing and an opening surface, and a combination of a pressure loss coefficient, an opening spacing, and an opening surface.

* * * * *